US009788843B2

(12) United States Patent
Teisen et al.

(10) Patent No.: US 9,788,843 B2
(45) Date of Patent: Oct. 17, 2017

(54) BONE ACCESS INSTRUMENT

(71) Applicant: DePuy Synthes Products, Inc., Raynham, MA (US)

(72) Inventors: Jacques Teisen, Oberdorf (CH); Rainer Ponzer, Oberdorf (CH)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 0 days.

(21) Appl. No.: 14/963,969

(22) Filed: Dec. 9, 2015

(65) Prior Publication Data

US 2016/0106441 A1 Apr. 21, 2016

Related U.S. Application Data

(63) Continuation of application No. 13/894,134, filed on May 14, 2013, now Pat. No. 9,226,756.

(60) Provisional application No. 61/646,708, filed on May 14, 2012.

(51) Int. Cl.
*A61B 17/16* (2006.01)
*A61B 17/34* (2006.01)
*A61B 17/17* (2006.01)

(52) U.S. Cl.
CPC ...... *A61B 17/1615* (2013.01); *A61B 17/1604* (2013.01); *A61B 17/1637* (2013.01); *A61B 17/1671* (2013.01); *A61B 17/1757* (2013.01); *A61B 17/3472* (2013.01)

(58) Field of Classification Search
CPC ............ A61B 17/1615; A61B 17/1671; A61B 17/1604; A61B 17/3472
See application file for complete search history.

(56) References Cited

U.S. PATENT DOCUMENTS

| | | |
|---|---|---|
| 5,057,082 A | 10/1991 | Burchette, Jr. |
| 5,171,279 A | 12/1992 | Mathews |
| 5,242,443 A | 9/1993 | Kambin |
| 5,645,547 A | 7/1997 | Coleman |
| 5,676,681 A | 10/1997 | Yoon |
| 5,824,002 A | 10/1998 | Genetlia et al. |
| 5,928,243 A | 7/1999 | Guyer |
| 5,957,946 A | 9/1999 | Shuler et al. |
| 6,540,747 B1 | 4/2003 | Marino |
| 6,752,809 B2 | 6/2004 | Gorek |
| 6,890,308 B2 | 5/2005 | Islam |
| 7,166,107 B2 | 1/2007 | Anderson |
| 7,686,823 B2 | 3/2010 | Pingleton et al. |

(Continued)

OTHER PUBLICATIONS

International Search Report and Written Opinion (PCT/US2013/040983); Aug. 22, 2013.

*Primary Examiner* — Christopher Beccia
(74) *Attorney, Agent, or Firm* — Dunlap Codding, P.C.

(57) ABSTRACT

A bone access instrument comprising a shaft having a first shaft portion and a second shaft portion. The first shaft portion has a first diameter, a proximal end, a tapered distal end including at least three straight cutting edges being equally spaced circumferentially about the tapered distal end, and at least three flutes extending from the tapered distal end toward the proximal end in a parallel relationship to one another. The second shaft portion has a second diameter and a tapered distal end. The second diameter is less than the first diameter, and the second shaft portion extends axially from the distal end of the first shaft portion.

11 Claims, 9 Drawing Sheets

(56) References Cited

U.S. PATENT DOCUMENTS

| | | |
|---|---|---|
| 7,695,467 B2 | 4/2010 | Breznock et al. |
| 7,846,164 B2 | 12/2010 | Castillo et al. |
| 7,892,207 B2 | 2/2011 | Simonton et al. |
| 8,002,775 B2 | 8/2011 | McKay |
| 8,070,767 B2 | 12/2011 | Smith |
| 8,157,847 B2 | 4/2012 | Anderson |
| 8,167,884 B2 | 5/2012 | Pacheco |
| 8,214,014 B2 | 7/2012 | Pacheco |
| 2004/0243137 A1 | 12/2004 | Gorek |
| 2005/0273107 A1 | 12/2005 | Stevens |
| 2007/0255281 A1 | 11/2007 | Simonton et al. |
| 2007/0270896 A1 | 11/2007 | Perez-Cruet |
| 2008/0045965 A1 | 2/2008 | Miller et al. |
| 2008/0154304 A1* | 6/2008 | Crawford .......... A61B 17/1615 606/246 |
| 2008/0161845 A1 | 7/2008 | Murakami et al. |
| 2008/0306405 A1 | 12/2008 | Masseglia et al. |
| 2009/0024130 A1 | 1/2009 | Lombardo |
| 2009/0228012 A1 | 9/2009 | Gangii et al. |
| 2009/0312782 A1 | 12/2009 | Park |
| 2010/0145341 A1* | 6/2010 | Ranck ................ A61B 17/1615 606/80 |
| 2010/0318112 A1 | 12/2010 | Smith |
| 2011/0054537 A1 | 3/2011 | Miller et al. |
| 2011/0060343 A1 | 3/2011 | Scortecci |
| 2011/0152866 A1 | 6/2011 | Knutson |
| 2012/0035641 A1 | 2/2012 | Mazzolla et al. |

* cited by examiner

BONE ACCESS INSTRUMENT

CROSS-REFERENCE TO RELATED APPLICATIONS

This application is a continuation of U.S. Ser. No. 13/894,134, filed May 14, 2013; which claims the benefit of U.S. Provisional Application Ser. No. 61/646,708, filed May 14, 2012; the entirety of each being hereby expressly incorporated herein by reference.

BACKGROUND

The spinal column of bones, or spine, is highly complex in that it includes over twenty vertebral bones, called vertebrae, coupled to one another so as to support the body and to house and protect critical elements of the nervous system. In addition, the spine is a highly flexible structure, capable of a high degree of curvature and twist in multiple directions. The most flexible of all the regions of the spine is the cervical spine. The bones and connective tissue of an adult human spine are coupled sequentially to one another by a tri-joint complex which consists of an anterior disc and the two posterior facet joints. The vertebral bodies of the vertebrae are separated and cushioned by soft yet resilient spacers referred to as intervertebral discs. The vertebral bones of the spine are classified as cervical, thoracic, lumbar, and sacral, and defining vertebral levels, e.g., L3 for the third lumbar vertebral level. The cervical portion of the spine, which comprises the upper portion of the spine up to the base of the skull, includes the first seven vertebrae. The twelve intermediate bones comprise the thoracic vertebrae, and connect to the lower spine which comprises the five lumbar vertebrae. The base of the spine is the sacral bones (including the coccyx).

Genetic or developmental irregularities, trauma, chronic stress, tumors, and disease, such as osteoporosis or degenerative disc disease (DDD), are a few of the causes which can result in spinal pathologies for which treatment procedures and assemblies have been disclosed in the art. These procedures and assemblies may be classified as anterior, posterior, or lateral. As the classification suggests, posterior procedures and assemblies are either attached to, or access to the vertebral bodies is achieved from, the back of the spinal column (transpedicular) or the side of the spinal column (extrapedicular). Such procedures and assemblies may include, by way of example, immobilization (fusion) of multiple vertebrae with instruments, such as rods and screws, introduction of balloon-expandable stents into one or more vertebral bodies to restore the loss of height of fractured vertebral bodies, or the introduction of bone cement into one or more vertebral bodies to fix and stabilize traumatic, osteoporotic and pathological fractures of the vertebral bodies and thus relieve pain. In each case, the hard cortical bone is penetrated to gain access to the vertebral body cavity via a surgical instrument.

The typical vertebra includes two parts: an anterior (or front) segment, which is the vertebral body; and a posterior (or back) segment called the vertebral (neural) arch, which encloses the vertebral opening where the spinal cord is housed. The vertebral arch is formed by a pair of pedicles and a pair of laminae, and supports seven processes, four articular, two transverse, and one spinous. The pedicles are two relatively short, thick processes, which project dorsally (e.g., sideways) one on either side, from the upper part of the vertebral body at the junction of the posterior and lateral surfaces of the vertebral body. The pedicles function to connect the vertebral body to the vertebral arch. The pedicles are often used as a radiographic marker and entry point in a variety of spinal surgical procedures, and include a relatively thick layer of dense and hard cortical bone to provide structural strength to the vertebral arch.

A trend in spinal surgery is to perform surgery in a minimally invasive or minimal access fashion to avoid the considerable trauma of so-called open or "direct access" procedures that require large incisions to lay bare the lesion space to be treated. While significant strides are being made in this area of minimal invasive surgery (MIS) and percutaneous procedures, a risk exists (as it does in open procedures) that the pedicle may become breached, cracked, or otherwise compromised during a procedure. One period during a posterior procedure in which the risk of a pedicle breach is significant is during the process of initially accessing the pedicle.

Options for achieving initial access to a pedicle include the use of a guide wire, such as a Kirschner wire (or K-wire), or a trocar, by way of example. Each implement has its advantages and disadvantages. With respect to use of a K-wire, which is typically made from heavily cold drawn high-strength implant steel (such as 316L), this procedure includes inserting the K-wire to the target site and driving the K-wire into the pedicle, creating a guide for larger caliber instruments to slide on, such as a cannula or cannulated trocar. The main advantage of any K-wire is its relatively small diameter, typically in the range of 0.8-2.4 mm, that allow safe and easy repositioning in case of initial misplacement, however slight, by retracting the K-wire back to the bony surface, re-adjusting its angle of introduction, and piercing the cortical bone another time, taking a new and different trajectory through the pedicle (typically under the mandatory guidance of C-Arm X-ray fluoroscopy). While surgical procedures in the lumbar or thoracic spine call for K-wire diameters in the 2 mm range, cervical spine procedures call for K-wire diameters in the 1 mm range, due to the smaller dimensions of most features of the cervical vertebrae. The pedicle has been left relatively undamaged due to the small diameter of the K-wire. Due to the size and shape of the typical K-wire, notably the absence of any handle affixed to its proximal end, manipulation and maneuvering of the K-wire may be cumbersome or difficult, increasing the risk of breaching the anterior cortical wall, nerves, or large blood vessels (e.g., the aorta and the vena cava). Especially when guiding larger caliber instruments, such as a cannula or a cannulated trocar over the K-wire, the relatively large surface area between the outer diameter of the K-wire and the inner diameters of the larger caliber tubular instruments often leads to frictional resistance in pushing the entire instrument assembly further distally, or anteriorly, towards the vertebral body, increasing the risk of inadvertently pushing the K-wire forward towards the anterior wall of the vertebral body. This risk is exasperated when the K-wire is not straight anymore, but slightly bent inside the cannulated instruments sliding on the K-wire. On the other hand, K-wires have also been known to protrude posteriorly out of the larger caliber tubular instruments and pierce the surgeon's surgical gloves, potentially injuring or infecting the surgeon.

A trocar has the advantage of being a one-step system and having its metal shaft affixed to an ergonomic plastic handle. However, because of its relatively larger diameter, more force is generally required to cause the trocar to pierce the cortical wall of the vertebral body, especially the pedicle that represents the longest distance of dense bone to go through (typically in a range of 2-50 mm, depending on the vertebral level) and is considered to be the strongest part of the vertebra. As such, a risk exists of breaking too much cortical bone (e.g., high risk of damaging or destroying the pedicle) when attempting to have the large caliber trocar eventually reach the cancellous bone inner region of the vertebral body and position any cannula or working sleeve for implant delivery. The risk of pedicle damage is exasperated when the user is trying to re-adjust the trajectory of the trocar either while the trocar is in the pedicle or by retracting the trocar to the bony surface, then re-adjusting the angle (typically under the guidance of C-arm X-ray fluoroscopy) before embarking on the new trajectory through the pedicle. Also, when the piercing tip of the trocar breaks through the cortical wall, resistance to penetration suddenly significantly decreases and the tip may breach the anterior cortical wall or damage the pedicle and/or adjacent nerves or blood vessels.

Another known surgical technique is the Jamshidi bone marrow biopsy technique, which uses special instruments called Jamshidi needles to pierce a cortical bone and to extract bone marrow from the bone. Jamshidi needles have found wide use in other surgical techniques, such as pedicle screw placement, for example.

Jamshidi needles may be used to locate the pedicle and the screw entry point and to break the cortex of the pedicle. A K-wire may be inserted through the Jamshidi hollow needle into the pedicle and the vertebral body, the Jamshidi needle acting as a guide tube for the K-wire. Cannulated screws can then be inserted over the K-wire safely, the K-wire acting as a guide wire for the cannulated screws. In the cervical spine lateral mass screws or hooks are more common, because pedicle screw placement in the cervical spine is challenging. The pedicles are rather narrow and therefore landmark identification and visualization is challenging when inserting pedicle screws. Different techniques can be used for pedicle screw placement in the cervical spine. Techniques are going from K-wire placement first under fluoroscopic control, to direct drilling with or without navigation. Due to the small screw diameter, the possible cannulation of the screw is rather small, and therefore the K-wire used typically has a small diameter as well. K-wires with small diameters bend easily and are difficult to guide. If the K-wires are bent, there is an increased risk of pushing the K-wire forward too much with the following surgical steps.

As an alternative technique pedicle probes and drills can be used. But because bigger diameters probes and drills are used and the pedicles are rather narrow in the cervical spine, this is very demanding without navigation.

In the lumbar and thoracic spine Jamshidi needles are often used to prepare the pedicle prior to screw insertion or vertebral augmentation procedures such as bone cement vertebroplasty, balloon kyphoplasty, or vertebral body stenting. Due to the narrow pedicles in the cervical spine the Jamshidi needles bear the risk of destroying the pedicle when pushing the Jamshidi needle into the bone. If an asymmetrical (e.g. beveled) tip is used, the Jamshidi needle also tends to go to the side and may over penetrate or penetrate out of the pedicle.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals may refer to the same or similar elements for consistency. For purposes of clarity, not every component may be labeled in every drawing. Certain features and certain views of the figures may be shown exaggerated in scale or in schematic in the interest of clarity and conciseness. In the drawings.

DETAILED DESCRIPTION OF EXEMPLARY EMBODIMENTS

Figure 1:
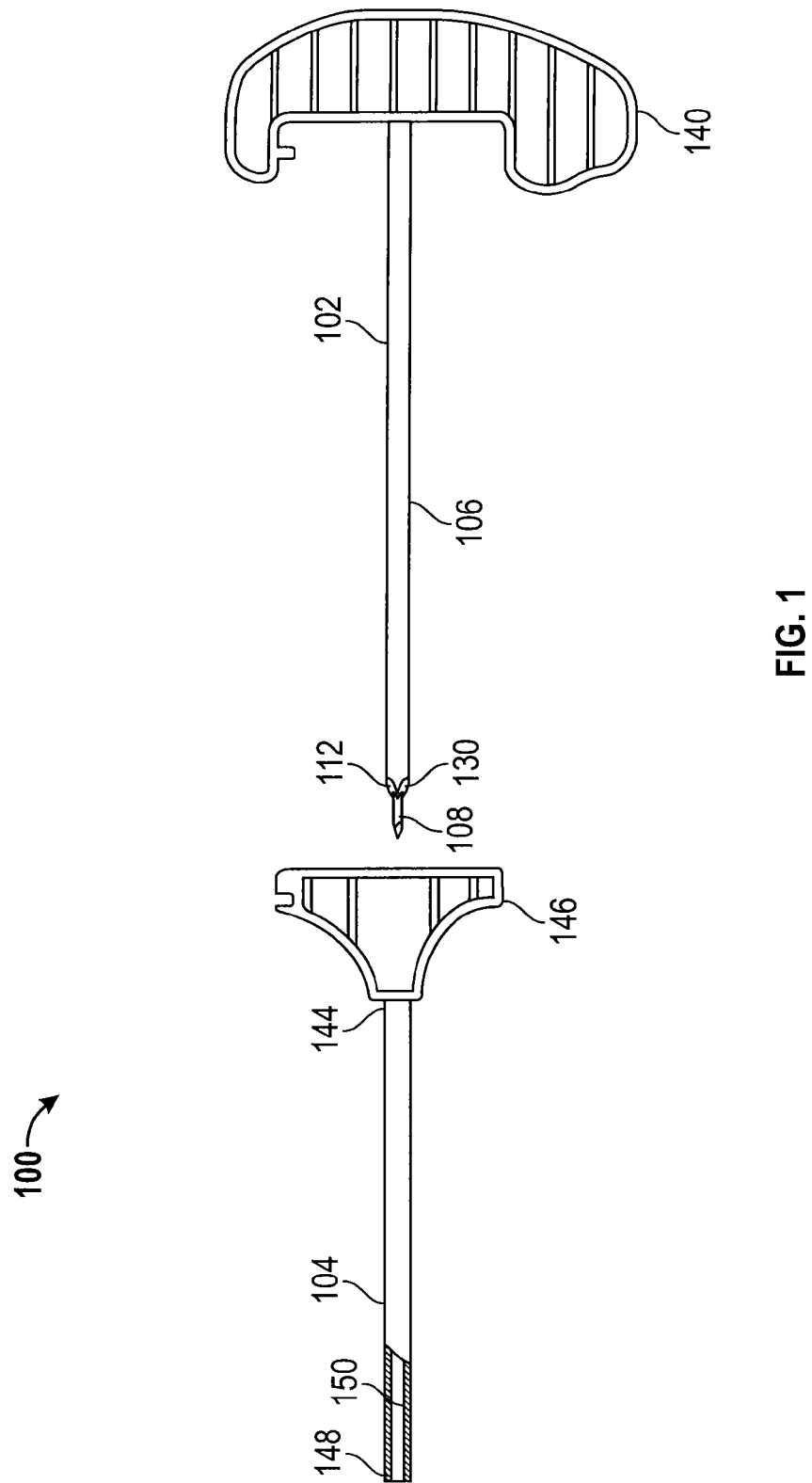
FIG. 1 is an exploded, partially cutaway, elevational view a bone access instrument constructed in accordance with the inventive concepts disclosed herein.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts disclosed and claimed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Throughout this disclosure and the claims, the terms "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, or combinations thereof, for example.

The use of the term "at least one" will be understood to include one as well as any quantity more than one, including but not limited to each of, 2, 3, 4, 5, 10, 15, 20, 30, 40, 50, 100, and all integers therebetween. The term "at least one" may extend up to 100 or 1000 or more, depending on the term to which it is attached; in addition, the quantities of 100/1000 are not to be considered limiting, as higher limits may also produce satisfactory results. Singular terms shall include pluralities and plural terms shall include the singular unless indicated otherwise.

The term "or combinations thereof" as used herein refers to all permutations and/or combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 2:
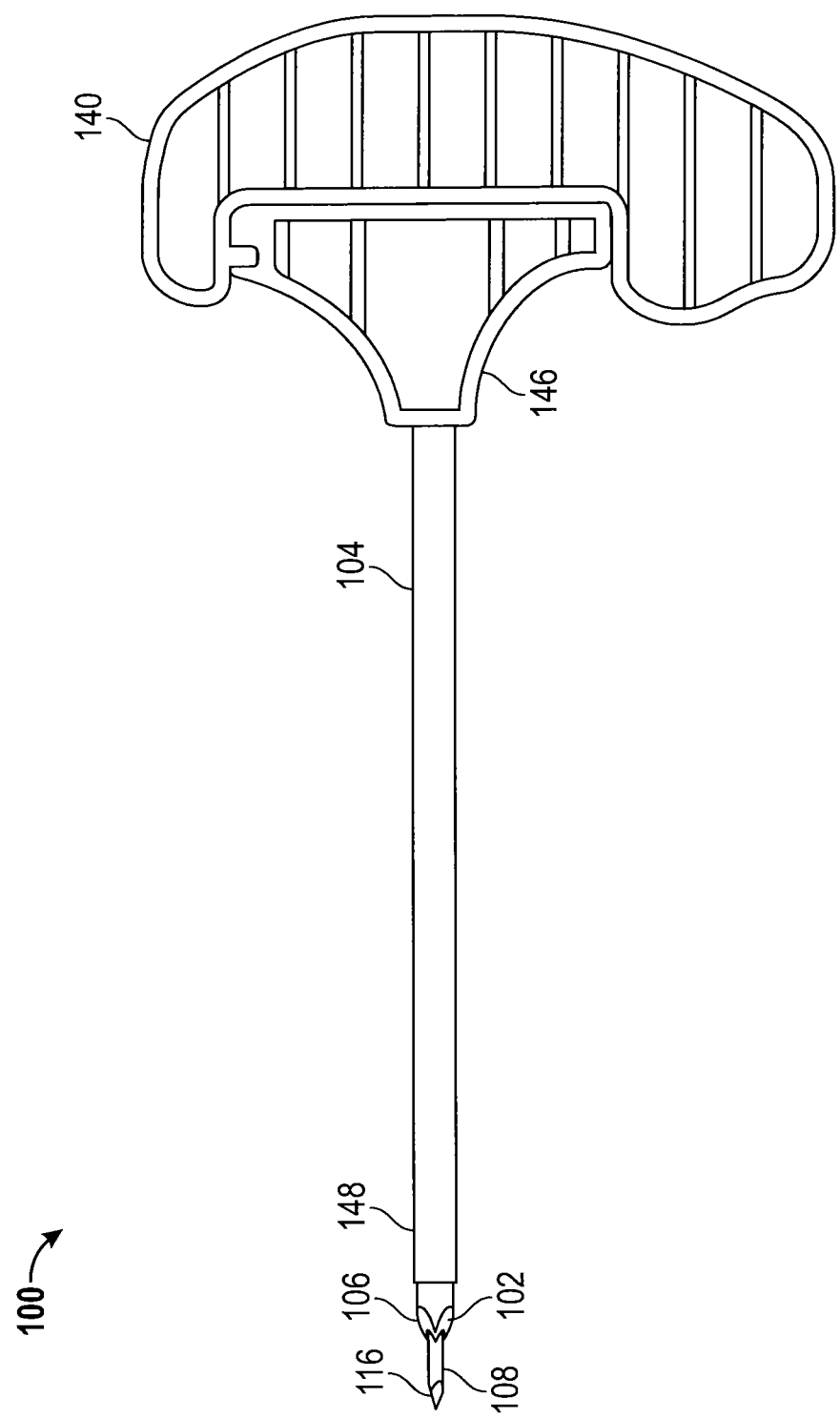
FIG. 2 is an assembled, elevational view of the bone access instrument of FIG. 1
Figure 3:
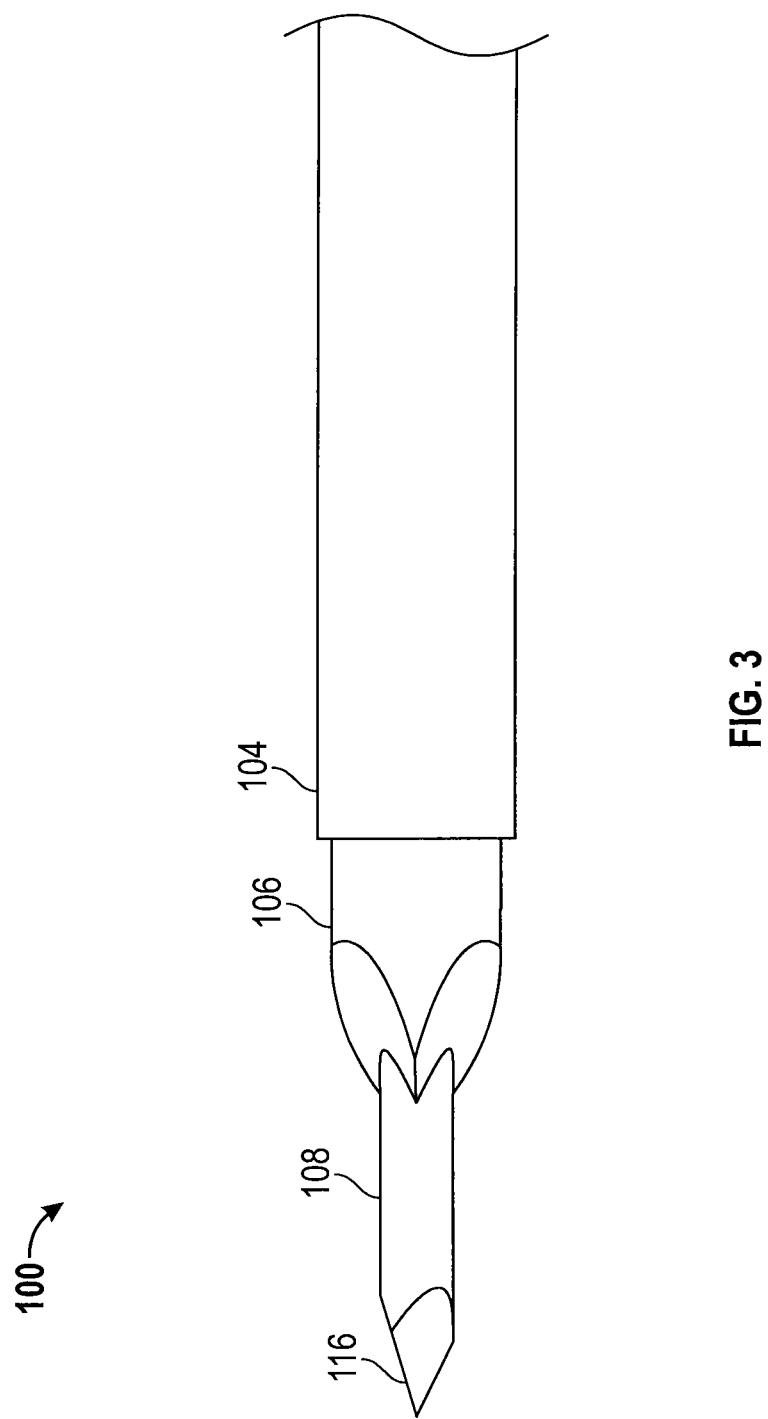
FIG. 3 is an enlarged, elevational view of a distal end of the bone access instrument of FIG. 2.

Referring now to FIGS. 1-3, one embodiment of a bone access instrument 100 constructed in accordance with the inventive concepts disclosed herein is illustrated. The bone access instrument 100 includes a shaft 102 and a cannula 104. The shaft 102 and the cannula 104 may be formed of stainless steel or other rigid materials, for example.

The shaft 102 has a first shaft portion 106 and a second shaft portion 108. The first shaft portion 106 has a first diameter and a tapered distal end 112 with at least one cutting edge 130 formed thereon. The second shaft portion 108 has a second diameter and a tapered distal end 116. The second diameter is less than the first diameter, and the second shaft portion 108 extends from the tapered distal end 112 of the first shaft portion 106. The second shaft portion 108 is shown extending from the first shaft portion 106 in an axial relationship, but in some exemplary embodiments, the second shaft portion 108 may extend from the first shaft portion 106 in an offset relationship.

In one version, the first shaft portion 106 has a circular cross-section, and the second shaft portion 108 has a circular cross-section. The first diameter may be in a range of from about 3 mm to about 5 mm, and the second diameter may be provided typically with a diameter of 2 mm and be in a range of from about 1 mm to about 2 mm. In one exemplary embodiment, the ratio of the diameter of the second shaft portion 108 to the diameter of the first shaft portion 106 may be about 1 to 2. In another embodiment, the second shaft portion 108 may have a second diameter varying between about 0.3 and about 0.7 times the first diameter of the first shaft portion 106, for example.

By way of further example, the second shaft portion 108 may be provided with a length of about 20 mm (and being in a range of about 10-30 mm, reflecting typical anatomical lengths of a pedicle cortical bone) while the first shaft portion 106 may have a length of about 150 mm (the range being about 120-180 mm, the typical anatomical lengths between the skin incision site and the posterior wall of the vertebral body, e.g., just past the distal end of the pedicle).

The shaft 102 has been shown to have two different diameters. However, it should be appreciated that the shaft 102 may be provided with any number of shaft portions, each with a different diameter and having a tapered transition zone formed between adjacent shaft portions. For example, the shaft 102 may include a third shaft portion (not shown) that has a diameter in a range of about 6 mm.

To facilitate the piercing of a bone, the tapered distal end 116 of the second shaft portion 108 may form a sharp point. The sharp point may be configured in a variety of shapes, including a pyramidal and chisel. In one version, the tapered distal end 116 of the second shaft portion 108 may be tapered at an angle of about 20° from the longitudinal axis of the shaft 102.

The tapered distal end 112 of the first shaft portion 106 serves as a transition between the non-tapered portion of the second shaft portion 108 and the non-tapered portion of the first shaft portion 106. Similar to the tapered distal end 116 of the second shaft portion 108, the tapered distal end 112 of the first shaft portion 106 may be configured in a variety of shapes, including pyramidal and chisel. In one version, the tapered distal end 112 of the first shaft portion 106 may be three-sided and tapered at an angle of about 20° from the longitudinal axis of the shaft 102. In the version of the tapered distal end 112 with three sides, the three sides may be formed from three planar surfaces. The three planar surfaces may be similarly sized and shaped or may be composed of differing sizes, shapes, and angle.

Figure 4:
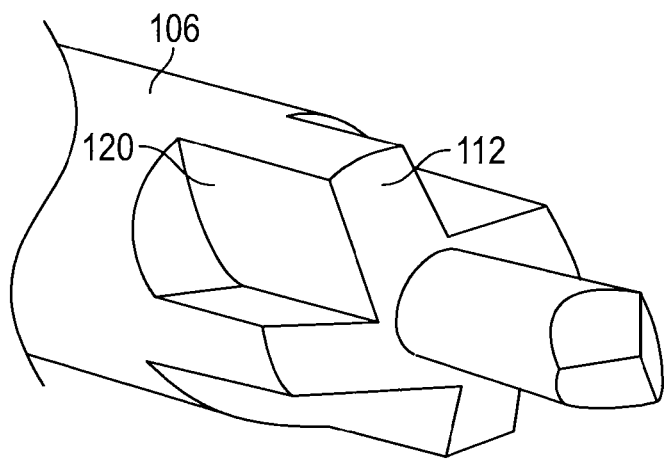
FIG. 4 is a perspective view of one embodiment of a shaft of a bone access instrument constructed in accordance with the inventive concepts disclosed herein.
Figure 5:
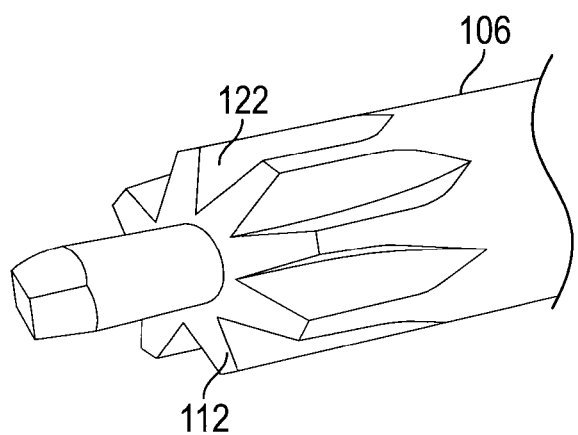
FIG. 5 is a perspective view of another embodiment of a shaft of a bone access instrument constructed in accordance with the inventive concepts disclosed herein.
Figure 6:
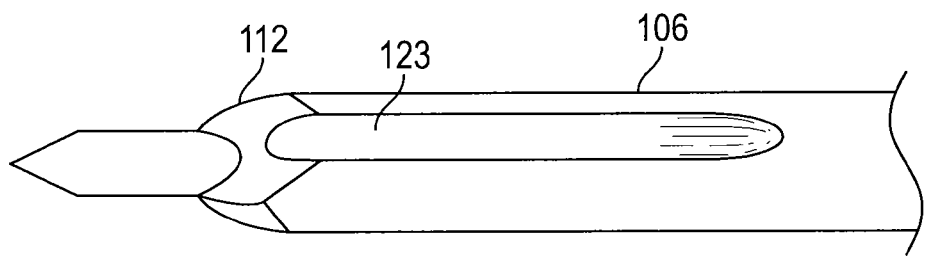
FIG. 6 is a perspective view of another embodiment of a shaft of a bone access instrument constructed in accordance with the inventive concepts disclosed herein.
Figure 7:
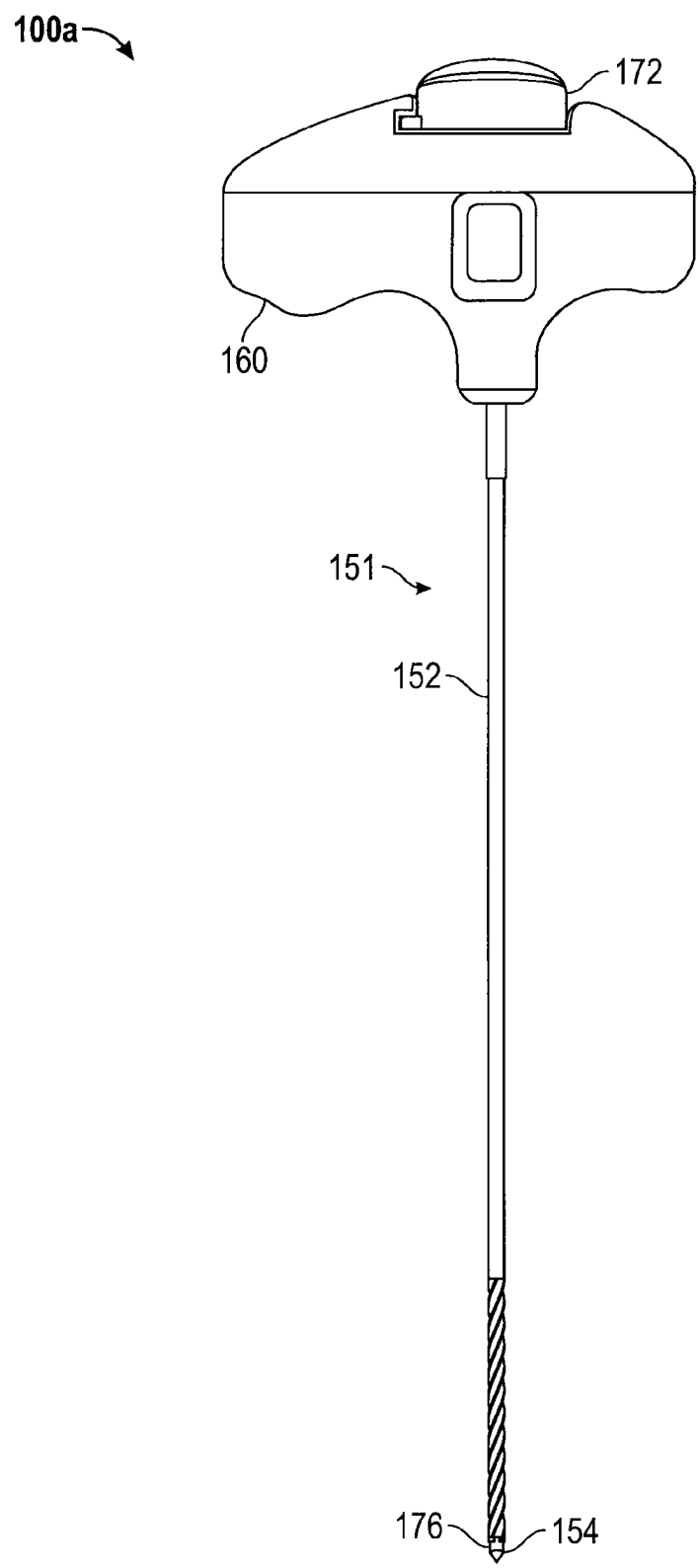
FIG. 7 is an assembled, elevational view of another embodiment of a bone access instrument constructed in accordance with the inventive concepts disclosed herein.

As illustrated in FIGS. 4-6, the first shaft portion 106, including the tapered distal end 112, may be provided with one or more flutes to form one or more cutting edges and to facilitate removal of bone debris. More specifically, in one version illustrated in FIG. 4, the first shaft portion 106 may be provided with helical flutes 120 similar to a drill bit. In versions illustrated in FIGS. 5 and 6, the first shaft portion 106 may be provided with a plurality of parallel flutes 122 and 123, respectively, (e.g., similar to a reamer) in its outer surface.

The first shaft portion 106 and the second shaft portion 108 may be formed from a single piece of material thereby forming a monolithic member. The second shaft portion 108 may alternatively be coupled to the first shaft portion 106 in any suitable way, such as by a press fit, or use of a suitable adhesive.

To facilitate manipulation of the shaft 102, the shaft 102 may be provided with a handle 140, such as a T-handle, on a proximal end of the first shaft portion 106.

The cannula 104 is a hollow cylinder with a bore 150 that provides an access corridor into the vertebral body when its distal end 148 is positioned into the vertebral body past its posterior wall and the shaft 102 is removed from the cannula 104. The cannula 104 has a proximal end 144 provided with a cannulated handle 146 and a distal end 148. The cannulated handle 146 may be configured to engage with the handle 140 of the shaft 102 so that the shaft 102 and cannula 104 may be manipulated as a unit or each may be manipulated separately.

In one embodiment, the bore 150 of the cannula 104 may be provided with a consistent inner diameter extending between the proximal end 144 and the distal end 148. The consistent inner diameter of the bore 150 of the cannula 104 may provide a uniform thickness to the hollow cylinder and a consistent useable diameter and largest possible working area, up to 2-3 mm, through which to insert the shaft 102 or other suitable instruments and implants.

As an example of the use of the bone access instrument 100, either a transpedicular or extrapedicular access may be selected depending on the anatomy of the vertebral body to be treated. The bone access instrument 100 allows the cannula 104 to be inserted into a vertebral body in a single step. The bone access instrument 100 is assembled by placing the shaft 102 in the cannula 104 and rotating the handle 140 of the shaft 102 into locking engagement with the handle 146 of the cannula 104. Under fluoroscopy, the second shaft portion 108 is inserted into the vertebral body until the tapered distal end 112 of the second shaft portion 108 is positioned on the bone. The shaft 102 is then driven to drive the second shaft portion 108 through the cortex until the tapered distal end 112 of the first shaft portion 106 engages the bone. To facilitate proper placement of the bone access instrument 100, once the second shaft portion 108 is inserted through the cortex, the contact of the tapered distal end 112 of the first shaft portion 106 may provide a tactile notification for the user inserting the bone access instrument 100. The increase in resistance of the tapered distal end 112 contacting the bone may signal the user to review the placement and orientation of the bone access instrument 100 including the second shaft portion 108 already inserted into the bone. The user may perform fluoroscopy, x-ray, or any other suitable imaging of the patient in order to determine the placement and orientation of the second shaft portion 108 within the bone. The user may then reposition the bone access instrument 100 or may continue insertion of the first shaft portion 106. The shaft 102 may then be further advanced so as to drive the tapered distal end 112 of the first shaft portion 106 through the cortex, as well as, the distal end 148 of the cannula 104 until the distal end 148 of the cannula 104 is seated approximately 1-4 mm into the vertebral body, i.e., just out of the pedicle and past the posterior wall of the vertebral body. After confirming proper positioning of the cannula 104, the shaft 102 is removed from the cannula 104 leaving the cannula 104 in the vertebral body.

Referring now to FIGS. 7-10, another embodiment of a bone access instrument 100a is illustrated. The bone access instrument 100a may be implemented and may function substantially similarly to the bone access instrument 100 described above. The bone access instrument 100a includes a shaft 151 that has a first shaft portion 152 and a second shaft portion 154. The first shaft portion 152 and the second shaft portion 154 are similar in construction to the first shaft portion 106 and the second shaft portion 108 described above except that the first shaft portion 152 is constructed to serve as a working cannula, and the second shaft portion 154 is configured to be slidably received in and removed from the first shaft portion 152 such that the second shaft portion 154 may be extended from the first shaft portion 152 in a manner similar to that described above with respect to the first shaft portion 106 and the second shaft portion 108, as well as selectively removed from the first shaft portion 152 so that the first shaft portion 152 may be used as an access corridor into a vertebral body.

The first shaft portion 152 has a proximal end 156, a distal end 158, and a bore 159 extending through the first shaft portion 152 from the proximal end 156 to the distal end 158. The bore 159 has a diameter such that the bore 159 may function as an access corridor into the vertebral body for an instrument, such as a K-wire, when the distal end 158 of the first shaft portion 152 is positioned in the vertebral body past its posterior wall. In one embodiment, the bore 159 may have a diameter of about 0.8-2.5 mm.

The outer diameter of the first shaft portion 152 may be any desired diameter, such as a diameter corresponding to the diameter of the second shaft portion 154, or a diameter larger than 1.8 mm, for example. Further, while the first shaft portion 152 is shown as being substantially cylindrical in shape, in some exemplary embodiments the first shaft portion 152 may be conical in shape and may have a varying diameter between the proximal end 156 and the distal end 158.

The proximal end 156 of the first shaft portion 152 may be provided with a handle 160. The handle 160 is cannulated to permit passage of the second shaft portion 154 into the bore 159 of the first shaft portion 152. The handle 160 may be provided with a cavity 162 configured to receive and engage a corresponding structure of the second shaft portion 154 in a manner to be described below.

Figure 11:
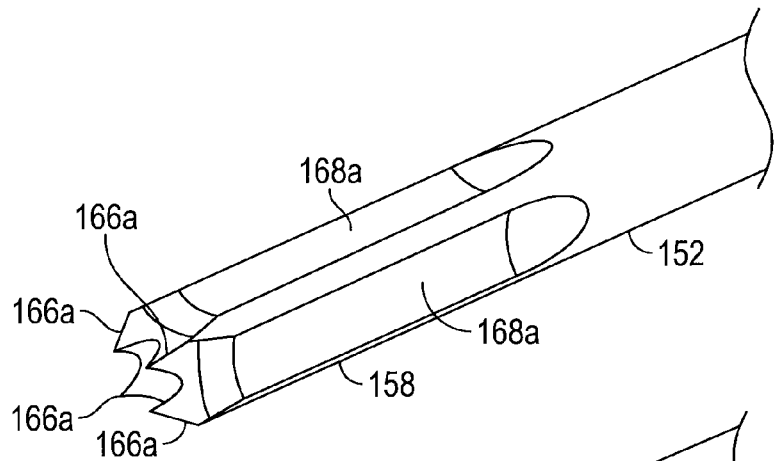
FIG. 11 is a perspective view of another embodiment of a distal end of a first shaft portion.
Figure 12:
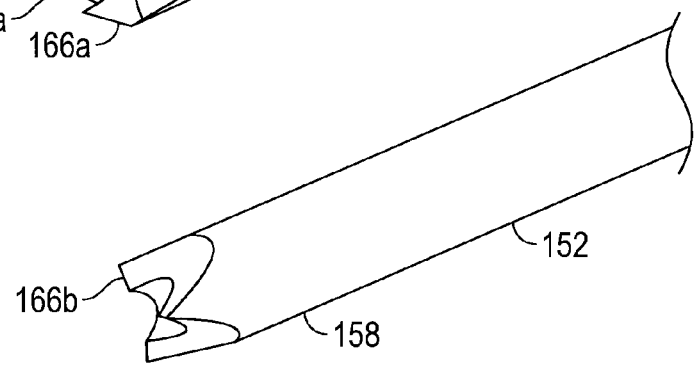
FIG. 12 is a perspective view of another embodiment of a distal end of a first shaft portion.
Figure 13:
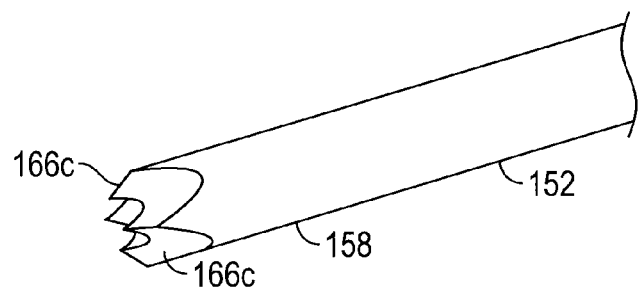
FIG. 13 is a perspective view of another embodiment of a distal end of a first shaft portion.
Figure 14:
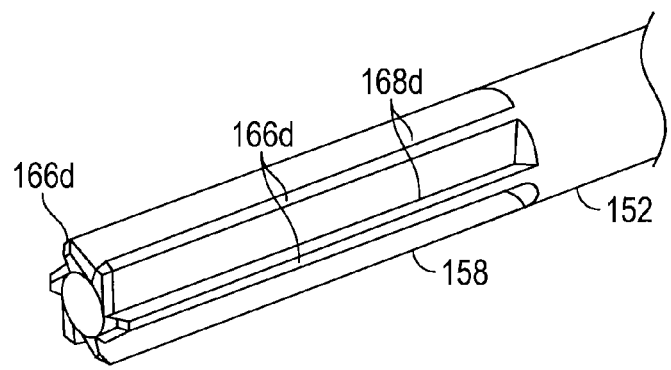
FIG. 14 is a perspective view of another embodiment of a distal end of a first shaft portion.

The distal end 158 of the first shaft portion 152 includes a cutting portion 164 similar to a drill, for example, to allow the distal end 158 of the first shaft portion 152 to function as a drill as will be appreciate by persons of ordinary skill in the art having the benefit of the instant disclosure. The cutting portion 164 includes cutting features that allow the distal end 158 of the first shaft portion 152 to drill, cut, or otherwise form an opening or a bore into a bone. The cutting features may include one or more cutting edges 166 configured to cut a bore into a bone and one or more flutes 168 configured to capture bone material and transporting the bone material out of the bore as the bone is cut by the cutting edges 166. In the exemplary embodiment shown in FIGS. 7-10, the cutting portion 164 is provided with four cutting edges 166 and four helical flutes 168. However, it is to be understood that any number of cutting edges and/or flutes may be implemented in a variety of configurations. For example, as illustrated in FIGS. 11, the distal end 158 of the first shaft portion 152 may include parallel cutting edges 166a and flutes 168a. As shown in FIGS. 12 and 13, the distal end 158 of the first shaft portion 152 may include three sided pyramidal cutting edges 166b or four sided pyramidal cutting edges 166c, by way of example. Also, as shown in FIG. 14, the distal end 158 of the first shaft portion 152 may include a plurality of angled and parallel cutting edges 166d, and flutes 168d, similar to a reamer.

Returning now to FIGS. 7-10, the cutting portion 164 extends from the distal end 158 of the first shaft portion 152 towards the proximal end 156 for a distance varying between about 20 mm and about 50 mm, for example, and may have an outer diameter varying between about 1.8 mm and about 4.5 mm. In some exemplary embodiments, the cutting portion 164 may be shorter than 20 mm or longer than 50 mm, or may have any desired length, including extending substantially from the proximal end 156 to the distal end 158 of the first shaft portion 152.

The flutes 168 may run out after any desired chosen length of the cutting portion 164 and a substantially smooth surface 170 (FIG. 8) may extend between the flutes 168 and the proximal end 156 of the first shaft portion 152, for example. In some exemplary embodiments, the cutting portion 164 of the first shaft portion 152 may have any number of cutting edges 166 and/or flutes 168, such as 2, 3, 5, or more than five cutting edges 166 and/or flutes 168.

Figure 8:
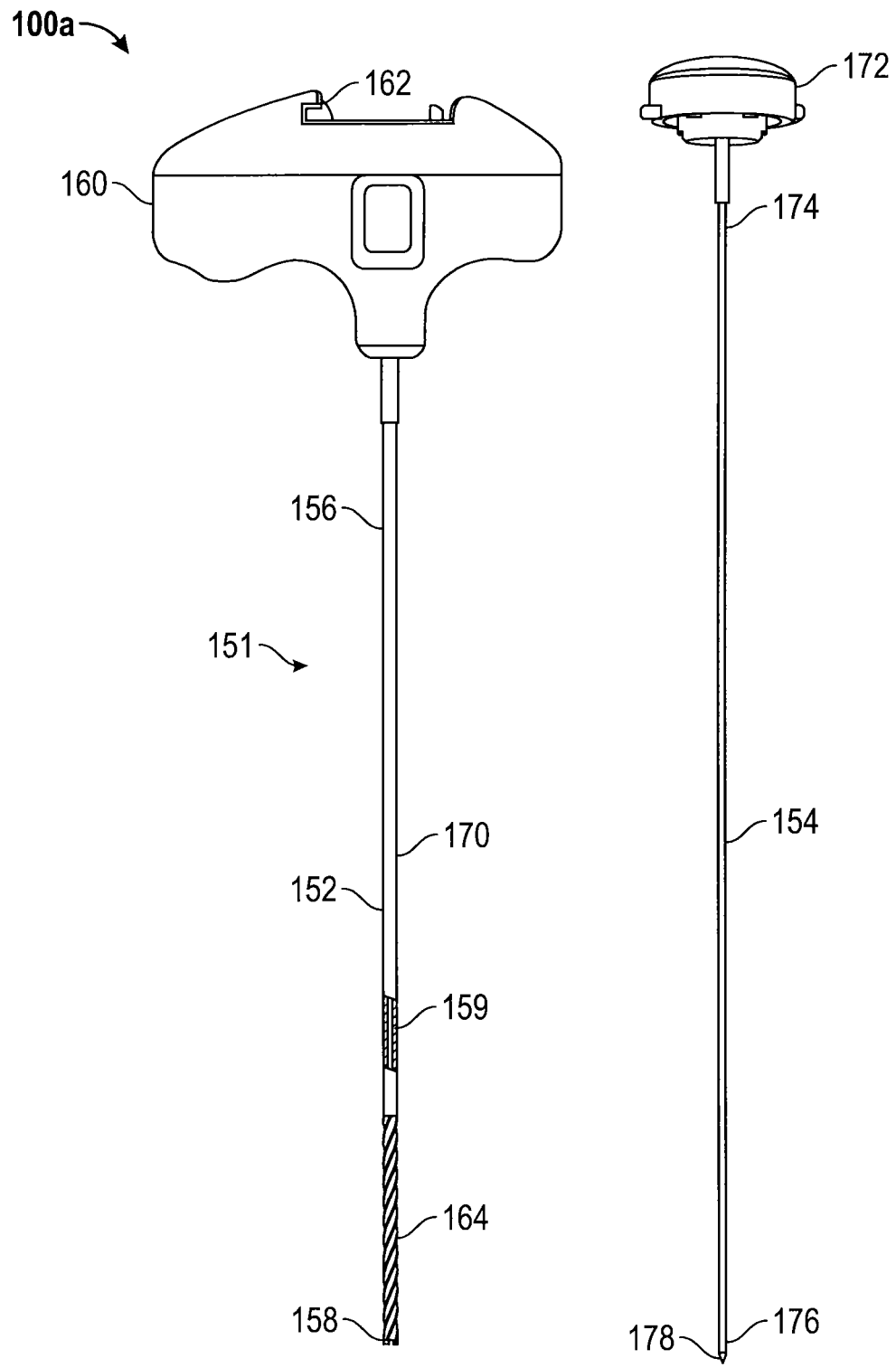
FIG. 8 is an exploded, partially cutaway, elevational view of the bone access instrument of FIG. 7.
Figure 9:
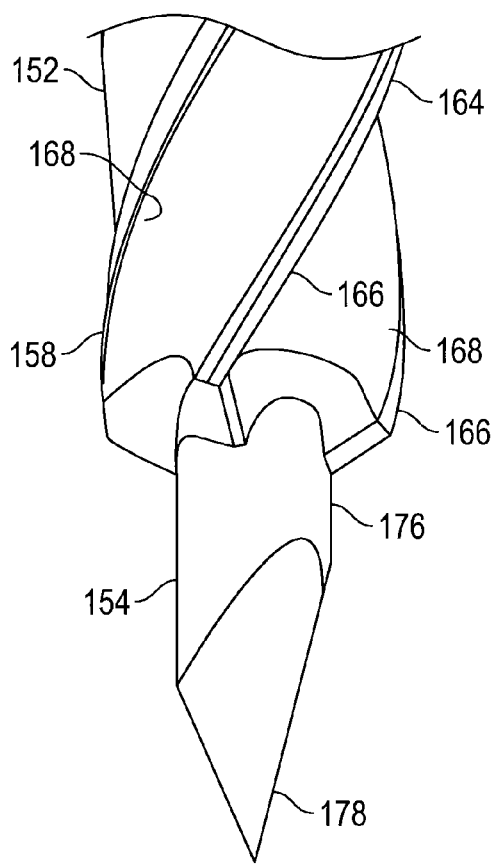
FIG. 9 is an enlarged perspective view of a distal end of the bone access instrument of FIG. 7.
Figure 10:
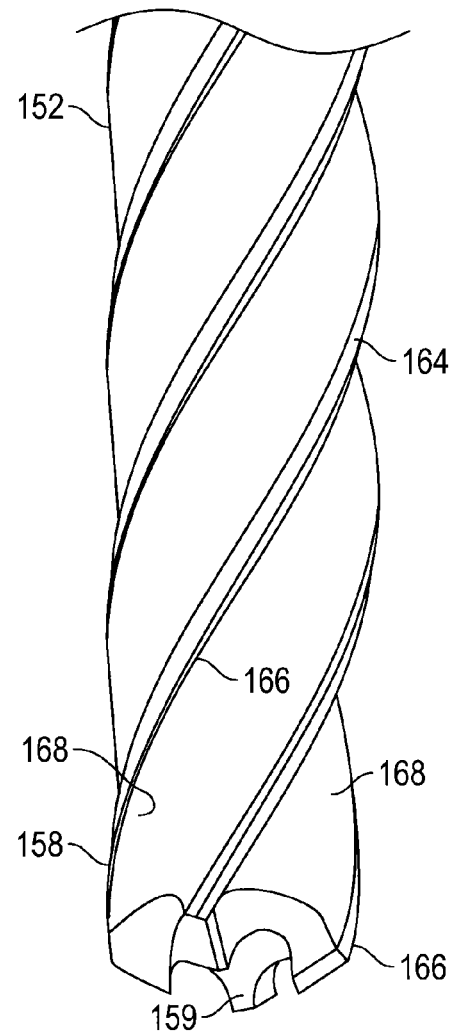
FIG. 10 is a perspective view of a distal end of a first shaft portion of the bone access instrument of FIG. 7.

Referring now to FIG. 8, the second shaft portion 154 has a proximal end 174 and a distal end 176. The second shaft portion 154 may be provided with a length such that the second shaft portion 154 extends past the distal end 158 of the first shaft portion 152 a distance ranging from about 1 mm to about 5 mm. The second shaft portion 154 may have a diameter of about 1.4 mm, although any diameter may be implemented. In some exemplary embodiments, the diameter of the second shaft portion 154 may vary between about 0.8 mm and about 2.5 mm, while in some exemplary embodiments the second shaft portion 154 may have a diameter smaller than 0.8 mm.

The proximal end 174 of the second shaft portion 154 may be provided with a knob or handle 172 which is configured to be received in the cavity 162 of the handle 160 of the first shaft portion 152. The knob 172 may be configured to allow a user to grasp the knob 172 and to separate the first shaft portion 152 and the second shaft portion 154 from one another, such as by removing the second shaft portion 154 from the bore 159, for example. The knob 172 may be permanently and substantially fixed to the proximal end 174 of the second shaft portion 154 so that the knob 172 is substantially centered relative to the second shaft portion 154, for example. The knob 172 may be attached to the proximal end 174 of the second shaft portion 154 substantially permanently, or such that the knob 172 may be disconnected and reconnected to the second shaft portion 154. In some exemplary embodiments, the second shaft portion 154 and the knob 172 may be formed as a unitary component.

The knob 172 is configured to lockingly engage the handle 160 of the first shaft portion 152 to enable the second shaft portion 154 and the first shaft portion 152 to lock or engage with one another. In some exemplary embodiments, the knob 172 and the handle 160 may be substantially radiolucent, to allow for an en face view approach, where the fluoroscopy view direction is aligned in axial direction of the instruments, and the metallic instruments thus appear just as a radiopaque spot on the fluoroscopy screen. As described above, when the knob 172 of the second shaft portion 154 is inserted and engages with the handle 160 of the first shaft portion 152, the distal end 176 of the second shaft portion 154 protrudes past the distal end 158 of the first shaft portion 152 at a distance varying from about 1 mm to about 5 mm, for example.

The handle 160 of the first shaft portion 152 is configured to be grasped by a user and to lock or otherwise engage with the knob 172 of the second shaft portion 154, so that the knob 172 and the handle 160 may lock with or otherwise engage one another so as to engage the first shaft portion 152 and the second shaft portion 154 to one another, for example. The handle 160 and the knob 172 may have any desired corresponding locking or engagement features, such as notches and recesses, prongs, surfaces, or combinations thereof, allowing the handle 160 and the knob 172 to lock with or otherwise engage one another, such as via being locked, snapped, press-fitted, inserted, clicked, or otherwise engaged with one another. In some exemplary embodiments, another component, such as a fastener, a bracket, a clamp, a vice, a retainer, a flange, a bayonet lock, a cam lock, a quick lock, a Luer lock, or any other desired component may be used to engage the handle 160 and the knob 172 with one another, as will be appreciated by a person of ordinary skill in the art having the benefit of the instant disclosure.

The distal end 176 of the second shaft portion 154 is configured to form a tip 178 for piercing bone. The tip 178 may be implemented and may function substantially similarly to the sharp point of the tapered distal end 116 as described above. The tip 178 is shown as being substantially centered relative to a longitudinal axis of the second shaft portion 154, but it is to be understood that in some exemplary embodiments more than one tip 178 may be implemented, and in some exemplary embodiments the tip 178 may be laterally offset or angled at any desired angle relative to the longitudinal axis of the second shaft portion 154. Further, in some exemplary embodiments, the second shaft portion 154 may have a blunt tip 178 and/or may have a tip 178 that is offset (e.g., beveled) from the longitudinal axis, for example.

In an exemplary embodiment of one method of use, pedicle screw placement using the bone access instrument 100a according to the inventive concepts disclosed herein may proceed as follows. The assembled instrument 100a, with the first shaft portion 152 and the second shaft portion 154 locked or otherwise engaged or joined together so that the tip 178 of the second shaft portion 154 extends past the distal end 158 of the first shaft portion 152 may be used to identify the correct entry point for safe pedicle screw placement. As will be appreciated by a person of ordinary skill in the art having the benefit of the instant disclosure, there are multiple ways to find the correct entry point. In one exemplary embodiment, a C-Arm (e.g., a movable fluoroscopic system) is desirably in an oblique position so that a pedicle having a cortical bone portion and/or a cancellous bone portion can be seen in an axial direction, called the en face view. If the correct position is found, the pedicle may appear in the x-ray image as a white spot, for example. The tip 178 of second shaft portion 154 may be placed substantially onto this spot using x-ray imaging as guidance. It will be appreciated by those of ordinary skill in the art that the bone access instrument 100a may be employed with non-pedicle access approaches, such as laminar transarticular, facet, odontoid, and anterior pedicle.

When the position is found, the bone access instrument 100a may be brought into the correct trajectory. The C-Arm may remain in the same position. When the correct trajectory is set, only a small dark (black or white) point may be seen from the bone access instrument 100a when using x-ray imaging, for example. That point represents the only radiopaque metallic components of the device in the view along the longitudinal axis of the instrument.

This black spot may be aligned with and positioned over the white spot identified as the pedicle. If this position is achieved the instrument 100a can be advanced by pushing, under gentle oscillary or rotational motion, the instrument 100a towards the pedicle, as one would do with awls. The tip 178 of the second shaft portion 154 may be used to initially puncture the cortical bone of the pedicle in some exemplary embodiments. The instrument 100a may be rotated so that the cutting portion 168 of the first shaft portion 152 may cut or drill a bore or an opening into the pedicle so as to advance the first shaft portion 152 and/or the second shaft portion 154 of the instrument 100a at least partially into the pedicle. The bore may have any desired size, diameter, and depth, for example. A radiolucent holder may be used to hold the instrument 100a in place, for example. The cutting portion 168 of the first shaft portion 152 may be advanced through the cortical bone portion of the pedicle and/or at least partially past the cortical bone portion of the pedicle and into a cancellous portion of the pedicle and/or the vertebral body, for example.

For trajectory control purposes or to verify proper placement of the instrument 100a, one or more X-Ray images can be taken periodically or at any desired time (e.g., via the C-Arm). When the desired depth is reached into the pedicle, the second shaft portion 154 may be removed from the pedicle, such as by disengaging or unlocking the knob 172 from the handle 160 and sliding the second shaft portion 154 out of the bore 159 of the first shaft portion 152, for example. A K-wire can be inserted through the bore 159 of the first shaft portion 152 and into the bone manually, or by using any desired tool or power tool. When the K-wire is in place, the first shaft portion 152 of the instrument 100a may be removed, such as via sliding the first shaft portion 152 over the K-wire, for example. Any desired cannulated pedicle screw may then be tabbed or inserted over the K-wire and into the bore formed into the bone. The cannulated pedicle screw may be a self-tapping pedicle screw in some exemplary embodiments. The cannulated pedicle screw may have an outer diameter corresponding to the diameter of the instrument 100a, such as an outer diameter varying between 1.8-4.0 mm, and any desired inner diameter depending on the diameter of the K-wire used, for example. In some exemplary embodiments, the pedicle screw may have an outer diameter of about 4 mm. The pedicle screw may also have an inner diameter varying between about 0.8 mm and about 2.5 mm, depending, for example, on the diameter of the K-wire over which the pedicle screw is inserted.

As an alternative, the instrument 100a may include more than two pieces, including, for example, a first shaft portion 152 and two or more second shaft portions 154 configured to be at least partially inserted into the bore 159 of the first shaft portion 152. As will be appreciated by persons of ordinary skill in the art, different and larger diameter can be implemented with the instrument 100a and a bore with any desired diameter can be made by the instrument 100a in a pedicle, for example.

There are alternative methods to determine the entry point for the instrument 100a and the trajectory of the instrument 100a. The entry point and trajectory can also be identified by A-P plus lateral X-Ray, or navigation, for example. Direct identification with small incision or puncture is possible in combination with X-Ray.

An instrument 100a and methods according to exemplary embodiments of the inventive concepts disclosed herein may be used to place lateral mass screws as well. The instrument 100a may also be used to place C1-C2 screws in the cervical spine. The instrument 100a may be used in other anatomical regions like thoracic or lumbar spine, for example. In addition, components that allow adoption for navigation and for other screws, other than posterior pedicle screws, such as laminar transarticular, facet, odontoid, and anterior pedicle, are also possible with some exemplary embodiments of the inventive concepts disclosed herein.

Figure 15:
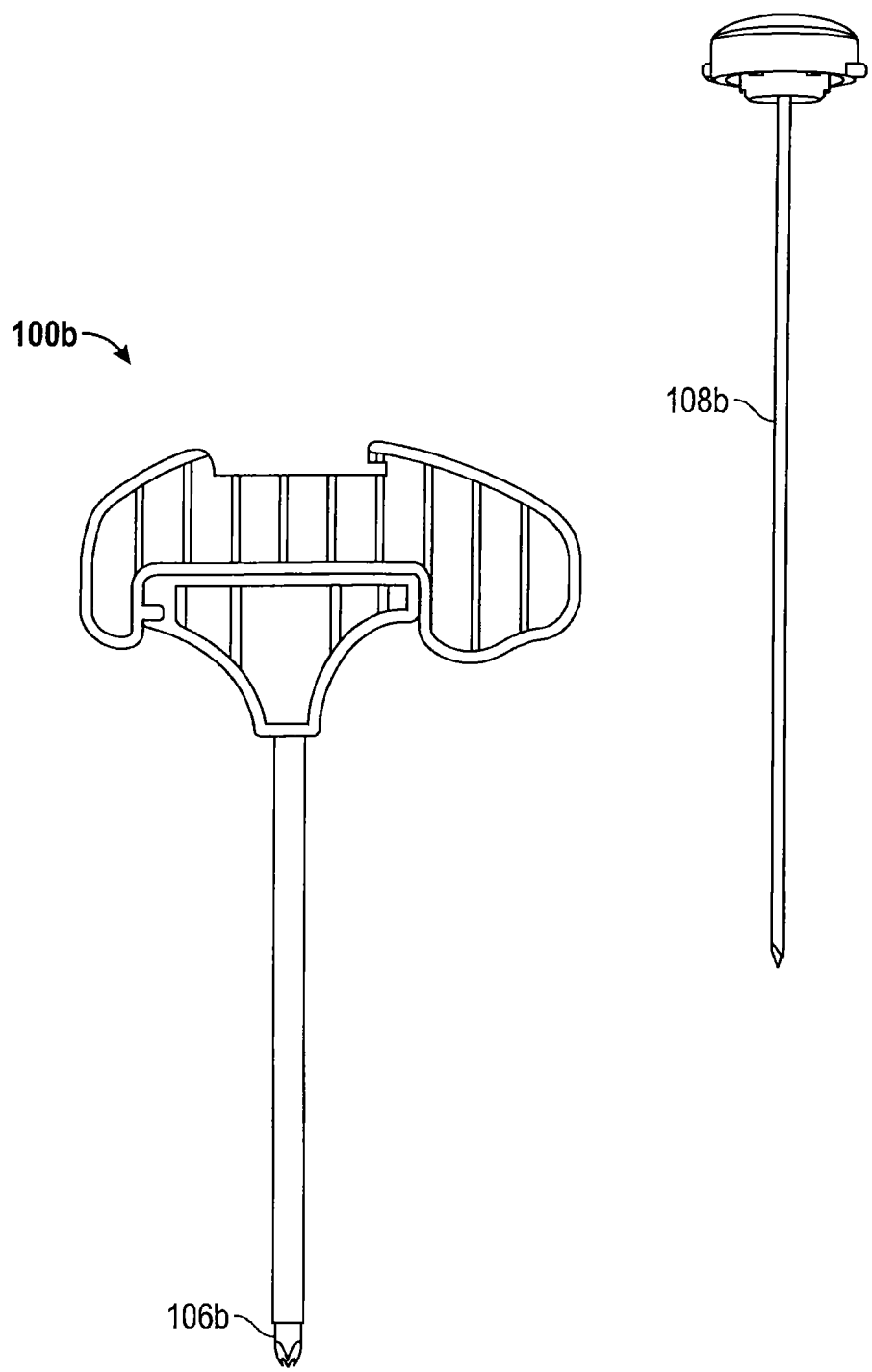
FIG. 15 is an exploded, elevational view another embodiment of a bone access instrument constructed in accordance with the inventive concepts disclosed herein.

FIG. 15 is an exploded, elevational view of another embodiment of a bone access instrument 100b constructed in accordance with the inventive concepts disclosed herein. The bone access instrument 100b is similar to the bone access instrument 100 described above, except that the bone access instrument 100b includes a shaft 102b with a first shaft portion 106b and a second shaft portion 108b. The second shaft portion 108b is configured to be slidably received in and removed from the first shaft portion 106b such that the second shaft portion 108b may be extended from the first shaft portion 106b in a manner similar to that described above with respect to the first shaft portion 106 and the second shaft portion 108, as well as selectively removed from the first shaft portion 106b so that the first shaft portion 106b may be used as an access corridor into a vertebral body.

From the above description, it is clear that the inventive concepts disclosed and claimed herein are well adapted to carry out the objects and to attain the advantages mentioned herein, as well as those inherent in the inventive concepts. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims. For example, bone access instruments 100 or 100a according to the inventive concepts disclosed herein may be employed for open access procedures and procedures other than those discussed herein.

What is claimed is:

1. A bone access instrument, comprising:
   a shaft having a first shaft portion and a second shaft portion,
   the first shaft portion having a first diameter, a proximal end, a tapered distal end, and at least three flutes extending from the tapered distal end toward the proximal end in a parallel relationship to one another, the tapered distal end including:
      at least three tapered planar surfaces which are similar in size and shape, and
      at least three straight cutting edges formed on the tapered distal end by interconnection of the planar surfaces and being equally spaced circumferentially about the tapered distal end,
   the second shaft portion having a second diameter and a tapered distal end, the second diameter being less than the first diameter and the second shaft portion extending axially from the tapered distal end of the first shaft portion.

2. The bone access instrument of claim 1, wherein the distal end of the second shaft portion forms a geometry that is selected from the group consisting of: sharp point, blunt point, diamond tip, beveled tip, asymmetrical tip, blade tip, paddle tip, crown tip, and drill tip.

3. The bone access instrument of claim 1, wherein the tapered distal end of the first shaft portion includes at least four straight cutting edges equally spaced circumferentially about the tapered distal end, and at least four flutes extending from the tapered distal end toward the proximal end in a parallel relationship to one another.

4. The bone access instrument of claim 3, wherein each of the at least four cutting edges is formed by the interconnection of planar surfaces.

5. The bone access instrument of claim 1 wherein the first shaft portion and the second shaft portion are formed as a monolithic member.

6. The bone access instrument of claim 1, wherein the first shaft portion and the second shaft portion are formed from at least two components.

7. The bone access instrument of claim 6, wherein the first shaft portion has a longitudinal bore extending therethrough, and wherein the second shaft portion is slidably positioned through the longitudinal bore.

8. The bone access instrument of claim 1, further comprising a cannula in which the shaft is slidably disposed, the cannula having a proximal end and a distal end, the cannula configured to receive the shaft such that the tapered distal end of the first shaft portion extends entirely beyond the distal end of the cannula.

9. The bone access instrument of claim 1, wherein the second shaft portion extends axially a distance in a range from about 2 mm to about 50 mm from the tapered distal end of the first shaft portion.

10. The bone access instrument of claim 1, wherein the diameter of the second shaft portion is 0.3-0.7 times the diameter of the first shaft portion.

11. The bone access instrument of claim 1, wherein the second diameter is less than the first diameter at a ratio of about 1:2.

\* \* \* \* \*